(12) United States Patent
Matsunaga et al.

(10) Patent No.: US 6,294,714 B1
(45) Date of Patent: Sep. 25, 2001

(54) METHOD FOR INTRODUCING A GENE INTO A PLANT USING AN ADVENTITIOUS BUD REDIFFERENTIATION GENE UNDER THE CONTROL OF A LIGHT-INDUCIBLE PROMOTER AS A SELECTABLE MARKER GENE, AND VECTOR FOR INTRODUCING A GENE INTO A PLANT USING THE SAME

(75) Inventors: Etsuko Matsunaga; Takehide Kasahara; Koichi Sugita; Hiroyasu Ebinuma, all of Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 0 days.

(21) Appl. No.: 09/354,305

(22) Filed: Jul. 16, 1999

(30) Foreign Application Priority Data

Jul. 16, 1998 (JP) .................................................. 10-202335
Jul. 12, 1999 (JP) .................................................. 11-197720

(51) Int. Cl.[7] .............................. C12N 5/04; C12N 15/09; C12N 15/31; C12N 15/82; A01H 5/00
(52) U.S. Cl. .......................... 800/290; 800/278; 800/288; 800/295; 435/69.1; 435/468; 435/419; 435/320.1; 435/430; 536/23.1; 536/23.7; 536/24.1
(58) Field of Search .................................... 800/290, 278, 800/295, 288; 435/69.1, 468, 419, 320.1, 430; 536/23.1, 23.7, 24.1

(56) References Cited

U.S. PATENT DOCUMENTS 5,965,791 * 10/1999 Ebinuma et al. ................. 800/205
5,994,629 * 10/1999 Bojsen et al. ..................... 800/298

OTHER PUBLICATIONS

Redig et al. Physiol. Plantarum, vol. 99, pp. 89–96, 1997.*

Hamdi et al. Plant Physiol. Biochem. vol. 33, No. 3, pp. 283–288, 1995.*

Schwarz–Sommer et al. Science, vol. 250, pp. 931–936, Nov. 1991.*

Medford et al. The Plant Cell, vol. 1, pp. 403–413, 1989.*

* cited by examiner

Primary Examiner—David T. Fox
Assistant Examiner—Medina A. Ibrahim
(74) Attorney, Agent, or Firm—Oblon, Spivak, McClelland, Maier & Neustadt, P.C.

(57) ABSTRACT

A method for introducing a gene into a plant, which comprises introducing a gene into a plant cell using a vector containing an adventitious shoot redifferentiation gene as a selectable marker gene under the control of a light-inducible promoter, and a vector for introducing a gene into a plant, which comprises a desired gene, an adventitious shoot redifferentiation gene as a selectable marker gene under the control of a light-inducible promoter, and a removable DNA element, wherein the selectable marker gene is positioned such that it behaves integrally with the removable DNA element, and wherein the desired gene is positioned such that it does not behave integrally with the removable DNA element.

21 Claims, 5 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 1

```
                                            -continued
ggatgttaat ggatacttct t                                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 2
gacaataatt ggtctctagt a                                                              21
```

METHOD FOR INTRODUCING A GENE INTO A PLANT USING AN ADVENTITIOUS BUD REDIFFERENTIATION GENE UNDER THE CONTROL OF A LIGHT-INDUCIBLE PROMOTER AS A SELECTABLE MARKER GENE, AND VECTOR FOR INTRODUCING A GENE INTO A PLANT USING THE SAME

BACKGROUND OF THE INVENTION

1. Field of the Invention

The present invention relates to a novel method for introducing a gene into a plant using genetic engineering techniques. Also, the present invention relates to a vector for introducing a gene into a plant used for the method.

2. Description of the Background

Transformation of microorganisms and cultured cells using genetic engineering is currently applied to the production of physiologically active substances useful as medicines and the like, and thus greatly contributes to the industry. In the field of plant breeding, industrial application of genetic engineering lags behind because the life cycles of plants are much longer than those of microorganisms and the like. However, since this technology enables a desired gene to be directly introduced into plants to be bred, it has the following advantages compared to classical breeding which requires multiple crossing: (a) it is possible to introduce only a characteristic to be improved; (b) it is possible to introduce characteristics of species other than plants (such microorganisms and the like); and (c) it is possible to greatly shorten the breeding period. Thus, a number of useful transgenic plants have been produced mainly in Europe and the U.S. and are now on the market.

Specifically, the production of transgenic plants requires the following three steps: (1) introducing the desired gene into the plant cell (including introduction of the same into the chromosomes, nucleus and the like); (2) selecting plant tissue made only of cells into which the desired gene has been introduced; and (3) regenerating a plant from the selected plant tissue. Among these steps, in selecting the desired transgenic tissue, generally, since it is difficult to confirm with the naked eye a tissue in which the desired gene is expressed (the tissue in which the desired gene is expressed is naturally a tissue constituted by cells into which the gene is introduced) without regenerating a plant, the desired gene is introduced into a plant cell together with a selectable marker gene of which expression can be easily detected at the stage of cell culturing, and the presence or absence of the expression of the selectable marker gene (namely, the presence or absence of the introduction of the selectable marker gene) is used as an index for the introduction of the desired gene. Examples of the selectable marker gene include a kanamycin-resistant gene (NPTII: neomycin phosphotransferase gene) and a hygromycin-resistant gene (hygromycin phosphotransferase gene) which impart resistance to antibiotics, a nopaline synthetase gene (NOS) and an octopine synthetase gene (OCS) which relate to amino acid synthesis, and a sulfonylurea-resistant gene (ALS: acetolactate synthetase gene) which imparts resistance to agricultural chemicals.

However, the expression of a selectable marker gene becomes a serious obstacle when its object is to apply such a transgenic plant to food. Namely, it is difficult to assure safety of the gene product obtained by the expression of the selectable marker gene on the human body. Consequently, when a transgenic plant produced using a selectable marker gene as an index is sold as food, it is necessary to carry out detailed examination on the effect of the gene product upon the human body. For example, although the NPTII gene has been already often used as a selectable marker gene at a laboratory level since the first half of 1980's, its gene product was approved by Food and Drug Administration (FDA) as a food additive for the first time in 1994, and transgenic plants to which the gene is introduced as a selectable marker gene have been used for food thereafter. However, uneasiness about such NPTII gene products is still present unavoidably at the essential level of consumers who actually eat these products.

Also, all of the genes which have so far been put into practical use as selectable marker genes, including the NPTII gene, are genes that contribute to the detoxication activity of plant cell growth inhibitors, so that selection of a tissue introduced with a desired gene is carried out by culturing the tissue using a medium containing such a growth inhibitor and evaluating the presence or absence of the expression of the selectable marker gene, namely resistance to the inhibitor, as an index. In that case, however, the presence of resistance, namely the ability of the plant tissue to grow in the presence of such an inhibitor, is merely a matter of degree, so that it is difficult to avoid undesirable influences of the culturing in the presence of such an inhibitor upon plant cells, and such influences are actually causing side effects, such as reduction of growth and redifferentiation ratio of the transgenic tissue due to decreased activity of the plant cells.

Furthermore, after selection of a transgenic tissue, expression of a selectable marker gene will cause considerable obstacles even at the level of researchers studying the plant breeding. That is, when a transgenic plant which has been produced by using a selectable marker gene is again introduced by another gene, introduction of the gene cannot be carried out using the same selectable-marker gene. In other words, since the selectable marker gene has been already present in the plant, the selectable marker gene is always expressed in the plant whether or not the new desired gene is introduced into the plant together with the selectable marker gene. Therefore, such a selectable marker gene can no longer be used as an index of the introduction of the new desired gene. Consequently, the number of times of repeated gene introducing into a certain plant is naturally restricted by the number of different selectable marker genes useful in the plant. However, kinds of selectable marker genes so far available are not so many. Additionally, all of the selectable marker genes are not necessarily useful in the plant of the object.

As a means for resolving these problems, the inventors of the present invention have previously provided a novel vector in International Publication No. WO 96/15252. This vector uses a morphological abnormality induction gene as a selectable marker gene which is present in plants in the natural world and whose safety upon the human body is secured to a certain degree. Additionally, when introduction of a gene into a plant is carried out using this vector, a transgenic tissue can be selected easily using its morphology as an index. That is, a tissue after a gene introduction treatment is cultured under appropriate conditions, and a tissue formed during the culturing showing abnormal morphology is detected and selected. It is not necessary to add an inhibitor which reduces plant cell activity to the medium during culturing. Also, when introduction of a gene into a plant is carried out using this vector in which the selectable marker gene is used in combination with a removable DNA element, a transgenic tissue from which influences of the selectable marker gene are completely removed can be obtained. Such a tissue can be obtained easily by merely carrying out its selection using morphology of the transgenic tissue as an index similar to the case of the above-described gene introduction.

However, even if gene introduction to a plant is carried out using such a vector, there is desire that improves working efficiency at the selection of the transgenic tissue.

That is, when a gene relating to production of a plant hormone is used as the morphological abnormality induction gene, the plant hormone produced by the gene expression in a transgenic cell migrates into its peripheral cells to provide influences indirectly, thus sometimes causing differentiation of adventitious shoots and adventitious roots from the nontransgenic cells which have received the influences. On the other hand, in the case of a tissue showing abnormal morphology generated from the transgenic cell which is directly influenced by the plant hormone, it is difficult in many cases to distinguish the abnormal morphology from normal adventitious shoots or roots at the initial stage of its generation. Accordingly, generally, the adventitious shoots or roots generated from the tissue after the gene introduction are separated and cultured, and then selection of the transgenic tissue is generally carried out. As a result of such culturing, morphological differences between a nontransgenic tissue and a transgenic tissue to such an extent that they can be distinguished with the naked eye, even in the case where these tissues are cultured as they are without separation. Then, the adventitious shoots and the like thus separated and cultured are actually occupied with the nontransgenic tissues at a marked ratio, and as a result, working efficiency at the selection of the transgenic tissue afterward is lowered.

SUMMARY OF THE INVENTION

Taking these problems in the case of the above-described vector into consideration, an object of the present invention is to reduce the ratio of the nontransgenic tissue to the adventitious shoot separated from the tissue after the gene introduction and to improve working efficiency at the selection of the transgenic tissue.

The present invention relates to a method for introducing a gene into a plant, which comprises introducing a gene into a plant cell using a vector containing an adventitious shoot redifferentiation gene as a selectable marker gene under the control of a light-inducible promoter.

Furthermore, the present invention relates to a vector for introducing a gene into a plant, which comprises a desired gene, an adventitious shoot redifferentiation gene as a selectable marker gene under the control of a light-inducible promoter, and a removable DNA element, wherein the selectable marker gene is positioned such that it behaves integrally with the removable DNA element, and wherein the desired gene is positioned such that it does not behave integrally with the removable DNA element.

DETAILED DESCRIPTION OF THE INVENTION

Figure 1:
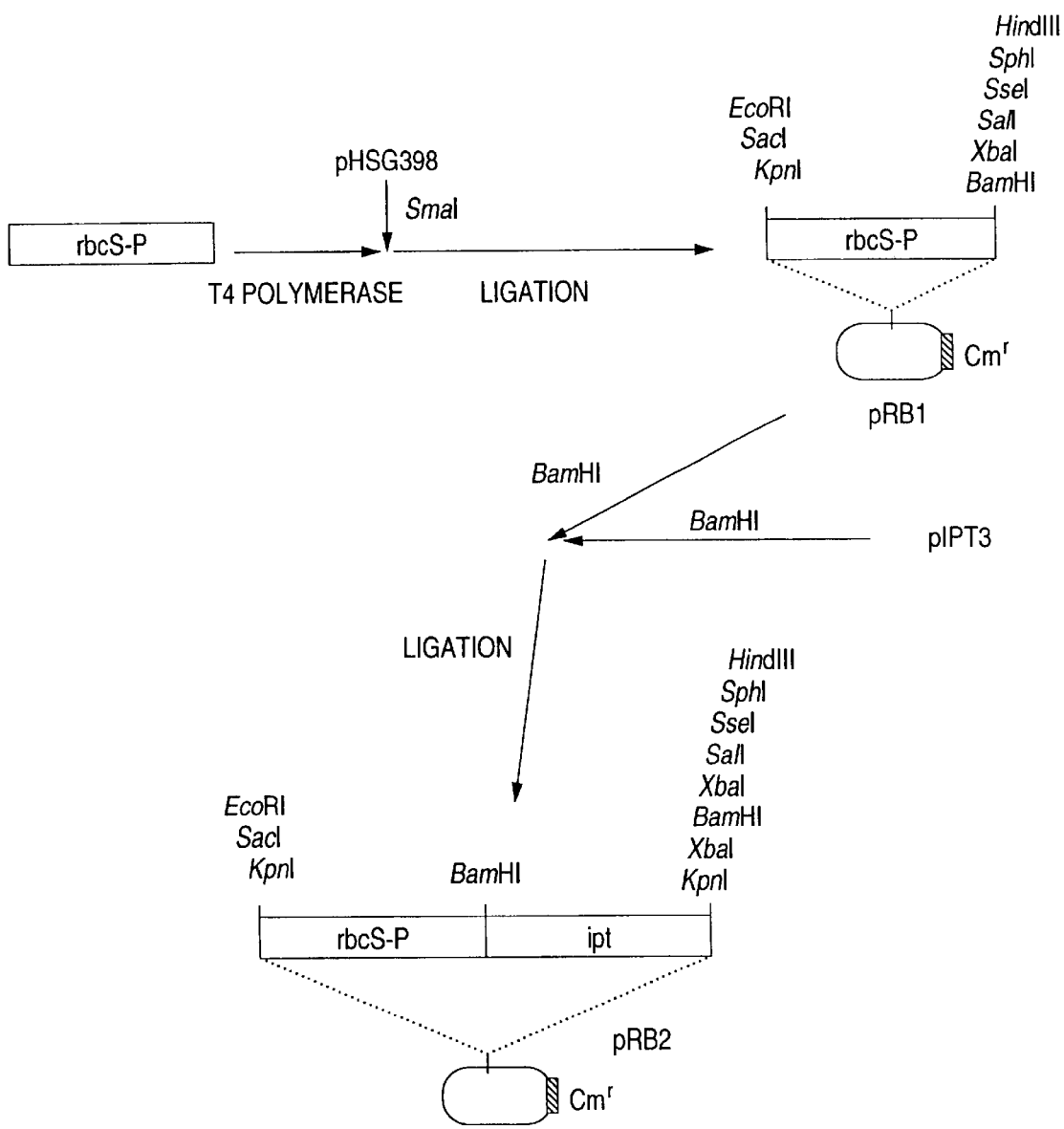
FIG. 1 is a view showing steps until construction of pRB2 in the pIPT20 construction scheme.

In order to solve the above-described problems, the inventors of the present invention have conducted intensive studies and found as a result of the efforts that, when an adventitious shoot redifferentiation gene is used as the morphological abnormality induction gene and the adventitious shoot redifferentiation gene under the control of a light-inducible promoter is introduced into a plant as a selectable marker gene, not only working efficiency at the selection of the transgenic tissues is improved due to reduced redifferentiation of adventitious shoots from nontransgenic cells but also redifferentiation of the transgenic cells becomes active in comparison with a case in which the same adventitious shoot redifferentiation gene under the control of other promoter is used as the selectable marker gene, so that the frequency of obtaining the transgenic tissue itself (gene introduction efficiency) also increases. The present invention has been accomplished on the basis of this finding.

The present invention will be discussed later in detail.

The term "adventitious shoot redifferentiation gene" as used herein means a gene having a function of inducing a redifferentiation of adventitious shoot from a plant tissue. Also, the term "adventitious shoot" means a shoot redifferentiated from a tissue from which a shoot should not be generated by nature. In the cell into which the adventitious shoot is introduced, adventitious shoot regeneration factors are produced by the expression of the newly introduced gene in addition to the adventitious regeneration factors originally produced in the cell, and therefore, the factors are overproduced so that finally a tissue having abnormal morphology, such as extreme shooty phenotype and the like, can be differentiated.

It is generally known that a plant hormone cytokinin is taking an important role in the redifferentiation of adventitious shoots. Thus, any one of the cytokinin-related genes can be used as the adventitious shoot redifferentiation gene, including cytokinin synthesis genes such as ipt gene (A. C. Smigocki and L. D. Owens, *Proc. Natl. Acad. Sci. USA*, 85: 5131 (1988)) derived from Agrobacterium tumefaciens (hereinafter referred to as "*A. tumefaciens*"), β-glucuronidase gene derived from *Escherichia coli* which is a gene which activates inactive cytokinin (Morten Joersbo and Finn T. Okkels, *Plant Cell Reports*, 16: 219–221 (1996)), and CKI1 gene derived from Arabidopsis thaliana which is considered to be a cytokinin receptor gene (Kakimoto T., *Science*, 274: 982–985 (1996)). In addition to these cytokinin-related genes, rol genes derived from *Agrobacterium rhizogenesis* (hereinafter referred to as "*A. rhizogenesis*") induce redifferentiation of adventitious shoots in a hormone-free medium, so that they can also be used as the adventitious shoot redifferentiation gene. Among these genes, the ipt gene is particularly preferred as the selectable marker gene to be used in the present invention because abnormal morphology induced thereafter can be detected easily.

According to the present invention, the adventitious shoot redifferentiation gene is used as the selectable marker gene under the control of a light-inducible promoter. Examples of the light-inducible promoters include a promoter of a ribulose 2-phosphate carboxylase small subunit gene (rbcS) (R.

Fluhr et al., *Proc. Natl. Acad. Sci. USA,* 83: 2358, 1986), a promoter of a fructose-1,6-bisphosphatase gene (JP-W-7-501921; the term "JP-W" as used herein means an "unexamined published Japanese international patent application"), and a promoter of a light-harvesting chlorophyll a/b binding protein gene (JP-A-5-89; the term "JP-A" as used herein means an "unexamined published Japanese patent application"), and the like.

When introduction of a gene into a plant is carried out using the above-described selectable marker gene, an adventitious shoot is differentiated from the transgenic cell by culturing the tissue after the gene introduction treatment under certain light conditions suitable for the activation of the used light-inducible promoter. When the adventitious shoot is cut, separated and cultured, eventually it shows abnormal morphology (e.g., extreme shooty phenotype which is an aggregate of disordered shoots with the apical dominance destroyed or an abnormally short shoot having thick internode), so that the transgenic tissue is selected using such a morphological change as an index in the present invention. When an adventitious shoot is cultured in a root-developing medium, the nontransgenic tissue develops a root but the transgenic tissue does not develop a root in most cases, so that selection of gene introduction can be carried out using the presence or absence of a root as an index. Also, because of the above-described reasons, a nontransgenic tissue is contaminated in the separated adventitious shoot to a certain degree but, according to the present invention, the ratio of such contamination can be reduced significantly so that working efficiency at the selection of the transgenic tissue can be improved, and additionally, a probability which can obtain the transgenic tissue per se (gene introduction efficiency) can also be improved.

It is reasonable in the present invention that when the nontransgenic tissue and the transgenic tissue can be distinguished without separately culturing these tissues, the transgenic tissue may be selected by culturing the tissue after the gene introduction as it is. In this case, the present invention exerts effects generally used that the gene introduction efficiency is improved and the transgenic tissue can be obtained at a high probability.

Introduction of a gene into a plant is carried out using a vector into which the selectable marker gene and a desired gene have been inserted. Kinds of the plant to be used for the gene introduction and the method for introducing the vector into plant cells are not particularly limited. The present invention can be applied to any plants into which a gene can be introduced by genetic engineering techniques. Introduction of the vector into plant cells can be carried out either by an indirect method in which the vector is introduced via a virus, such as cauliflower mosaic virus or gemini virus, or a bacterium, such as *A. tumefaciens* or *A. rhizogenes,* or by a direct method through a physical or chemical means, such as a microinjection method, an electroporation method, a polyethylene glycol method, or a particle gun method. Also, it has been considered generally that only dicotyledonous plants are infected with a microorganism of the genus Agrobacterium, but some cases have recently been reported in which gene introduction was carried out by infecting a monocotyledonous plant with such a microorganism (e.g., International Publication No. WO 94/00977).

Culturing of the tissue after gene introduction is carried out using a redifferentiation medium or transgenic tissue selection medium prepared by adding plant hormones (generally 0 to 10 mg/l of auxin and 0 to 10 mg/l of cytokinin) to an appropriate basic medium selected in response to the tissue to be used at a temperature suitable for growing of the tissue (generally from 20 to 30° C.) under light conditions. The conditions of the light irradiation, such as intensity of light, are optionally set by selecting conditions suitable for the activation of each light-inducible promoter which controls the adventitious shoot redifferentiation gene.

Effects of the above-described method for the introduction of a gene into a plant can be markedly improved by using, as the vector for the gene introduction, a vector for introducing a gene into a plant, which comprises a desired gene, an adventitious shoot redifferentiation gene under the control of a light-inducible promoter as a selectable marker gene, and a removable DNA element, wherein the selectable marker gene is positioned such that it behaves integrally with the removable DNA element, and wherein the desired gene is positioned such that it does not behave integrally with the removable DNA element.

The term "removable DNA element" as used herein means an element of a DNA sequence which itself is removable from the DNA wherein the DNA element exists and functions. In plants, a transposon present in a chromosome is known as this element. The structure, activity and behavior of transposons have been almost completely identified. For the transposon to function, two components are required in principle, an enzyme which is expressed from the gene present therein and which catalyzes the excision and transposition of the transposon itself (transposase), and DNA binding sequences which are present in the terminal region of the transposon and upon which the transposase acts. By these elements, the transposon is excised from the chromosome in which it exists, and is then usually transposed to a new position in the DNA. However, at a certain ratio, the transposon also disappears without being transposed. The present invention makes use of such a transposition error of the transposon.

The transposon can be one of two types, either an autonomous transposon or a non-autonomous transposon. The autonomous transposon maintains the two elements, the transposase and the DNA binding sequence. In the autonomous transposon, the transposase is expressed and binds to the DNA binding sequence for action, whereby the transposon is autonomously excised from the chromosome. The non-autonomous transposon retains the terminal DNA binding sequence to which the transposase is bound for action. In the non-autonomous transposon, the transposase gene undergoes mutation such that the transposase is not expressed; thus the transposon cannot be excised from the chromosome autonomously. However, when transposase is supplied to the non-autonomous transposon from the autonomous transposon or from an independent transposase gene, the non-autonomous transposon behaves similarly to the autonomous transposon.

Accordingly, in the present invention, both the autonomous and non-autonomous transposons can be used. For example, a non-autonomous transposon can be used by inserting therein a morphological abnormality induction gene and a transposase gene which is obtained from an autonomous transposon or synthesized.

Examples of the autonomous transposons include Ac and Spm isolated from maize (A. Gierl and H. Saedler, *Plant Mol. Biol.,* 19: 39, 1992). Ac can be obtained by digesting wx-m7 locus in the chromosome of the maize with restriction endonuclease Sau3A (U. Behrens et al., *Mol. Gen. Genet.,* 194: 346, 1984). This autonomous transposon is the most analyzed among plant transposons. In fact, the DNA sequence has already been determined (M. Mueller- Neumann et al., *Mol. Gen. Genet.*, 198: 19, 1984). Also, examples of non-autonomous transposons include Ds and dspm obtained by deleting the inner regions of Ac and Spm, respectively (H.-P. Döring and P. Starlinger, *Ann. Rev. Genet.*, 20: 175, 1986) and those isolated from many plants, other than maize, such as snapdragon, morning glory and the like (for example, Y. Inagaki et al., *Plant Cell*, 6: 375, 1994). When these transposons are introduced into chromosomes of exogenous plants, these transposons are also excised from a chromosome and transposed (for example, B. Baker et al., *Proc. Natl. Acad. Sci. USA*, 83: 4844, 1986).

Another removable DNA element, which is not present in plants, is an element derived from a site-specific recombination system. A site-specific recombination system consists of two elements, a recombination site (corresponding to the removable DNA element of the present invention) having a characteristic DNA sequence, and an enzyme (recombinase) that binds to the DNA sequence specifically and catalyzes the recombination between these DNA sequences if two or more of the sequences exist. When the two DNA sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted. The present invention utilizes the former excision. Both excision and inversion within the recombination site occur as a result of homologous recombination through the site-specific recombination system, which is different from the mechanism using the transposon. It is known that the recombinase gene is not necessarily present in the same DNA molecule, in which the recombination site exist. The recombinase gene only needs to be present in the same cell and expressed to excise or invert the region held by the two DNA sequences (N. L. Craig, *Annu. Rev. Genet.*, 22: 77, 1988).

At present, site-specific recombination systems have been identified in microorganisms such as phage, bacterium (e.g., *E. coli*), yeast and the like. Examples thereof include a Cre/lox system, a pSR1 system, a FLP system, a cer system, and a fim system (for example, N. L. Craig, *Annu. Rev. Genet.*, 22: 77, 1988). When the site-specific recombination system separated from these microorganisms with the use of a Cre/lox system derived from P1 phage (International Publication No. WO 93/01283) is introduced into organisms (including plants) different from the organism from which this system had been derived, it behaves in the same way as in the original organism. The site-specific recombination system of yeast (*Zygosaccharomyces rouxii*) (pSR1 system (H. Matsuzaki et al., *J. Bacteriology*, 172: 610, 1990)) can also be used in accordance with the present invention. This pSR1 system also maintains its inherent function in higher plants (H. Onouchi et al., *Nucleic Acid Res.*, 19: 6373, 1991).

When the selectable marker gene is used in combination with a removable DNA element, it can be inserted into a position where it is removed together with the removable DNA element. For example, when a transposon is used as the removable DNA element, this can be inserted into a position where has no influence on removing of the transposon, namely a position between upstream of the introduction gene promoter region and downstream of the terminal region to which the transferase is linked. Also, when a pSR1 system is used, this can be inserted into any position, so long as that the position is positioned within the region sandwiched by the recombination sequences and does not inhibit expression of the recombination enzyme.

When a gene is introduced into a plant using a vector having such a construction, the adventitious shoot redifferentiation gene used as a selectable marker gene loses its function after it is removed together with the removable DNA element at a certain probability from the DNA, such as plant chromosome, where they were once introduced and functioned. On the other hand, the desired gene which does not behave integrally with them remains on the same DNA.

Thus, when a gene is introduced into a plant using this vector, influence of the adventitious shoot redifferentiation gene used as a selectable marker gene is completely eliminated after selection of the transgenic tissue, so that a transgenic tissue and a plant having normal morphology can be obtained. Consequently, in order to carry out multiple introduction of genes into a plant, this vector can be used repeatedly without limitation by simply changing construction of the desired gene to be introduced. What is more, disappearance of the function of this adventitious shoot redifferentiation gene can be detected with the naked eye as morphological changes of the transgenic tissues similar to the case of the gene introduction, so that a tissue solely formed from the cells from which influence of the selectable marker gene is eliminated, in other words, a tissue solely formed from the cells in which only the desired gene remains in chromosome or the like and keeps its function, can be selected securely and easily by culturing the tissue. Also, multiple introduction of genes using this vector can be carried out efficiently, because not only the introduction step can be repeated unlimitedly but also it can be repeated at the stage of cultured tissue before regeneration of a complete plant. Additionally, a transgenic plant solely constituted by such cells alone can be obtained by simply regenerating the plant from a tissue selected by the above-described method without requiring a crossing process. As a matter of course, this vector exerts other effects of the present invention derived from the use of an adventitious shoot redifferentiation gene under the control of a light-inducible promoter as a selectable marker gene, for example, it is not necessary to use a cell growth inhibitor for the selection of transgenic tissues, redifferentiation of adventitious shoots from gene-non-introduced cells can be reduced, the gene introduction efficiency is improved, and the like.

In the present invention, most of the adventitious shoot redifferentiation genes to be used as the selectable marker gene are genes which contribute, for example, to the production of adventitious shoot redifferentiation factors, such as a plant hormone and the like, in the introduced cells, and such adventitious shoot redifferentiation factors will exert their influences upon not only the cells in which they are produced but also their peripheral cells free from the gene introduction, similar to the case observed by the use of the above-described previous vectors in which a plant hormone gene is used as the selectable marker gene. It seems that such a phenomenon is not related to the control of the adventitious shoot redifferentiation gene by the light-inducible promoter.

The reason is not clear why redifferentiation of a shoot from such a cell free from the gene introduction is inhibited in the present invention and the gene introduction efficiency is improved. However, it is assumed that the effects of the present invention are attained by the sharply amplified adventitious shoot redifferentiation acceleration activity in the transgenic cell in comparison with that in the gene-non-introduced cell, due to synergistic effects of certain facts that, as a reverse of the feature of the light-inducible promoter which is activated particularly strongly in green tissues, activity of the promoter is weak and expression of the adventitious shoot redifferentiation gene is depressed to a low level in a cell at the early stage of culturing even when the gene introduction is carried out by the present invention, that, since the adventitious shoot redifferentiation factor has a function of accelerating activity of the light-inducible promoter on the contrary, expression of the adventitious shoot redifferentiation gene under the control of the light-inducible promoter is rapidly activated and production of the factor sharply increases in the transgenic cell when this factor generated by the expression of the adventitious shoot redifferentiation gene reaches a certain level and that, as a result, production of the adventitious shoot redifferentiation factor by the transgenic cell becomes more prominent in the green tissue having high light-inducible promoter activity when the culturing is advanced to a certain stage, but the green tissue is also a tissue suitable for adventitious shoot redifferentiation.

It is also considered that, since the adventitious shoot redifferentiation is induced preferentially from a cell in which the gene is strongly expressed according to this mechanism, the desired gene is also expressed strongly in the transgenic tissue and plant derived from such an adventitious shoot.

Thus, according to the present invention, the redifferentiation of nontransgenic tissue, which is commonly observed when a gene is introduced into a plant using a vector in which a morphological abnormality induction gene is used as a selectable marker gene, is reduced. Consequently, working efficiency at the selection of the transgenic tissue is improved and the transgenic tissue and plant can be produced efficiently making use of other characteristics of such a vector.

Also, according to the present invention, the gene introduction efficiency per se into a plant is also improved so that the number of transgenic tissues obtained from one piece of tissue after the gene introduction treatment is sharply increased. Also, the plant tissues into which a gene is introduced by the present invention have a tendency to quicken redifferentiation of an adventitious shoot when compared with generally used methods. On the other hand, the desired gene is also expressed at a high level in the tissue into which the gene is introduced by the method of the present invention.

Moreover, the above effects are exerted particularly significantly in trees which are considered to be difficult in introducing a gene.

Additionally, a plant tissue and a plant from which influences of a selectable marker gene are completely removed and in which a desired gene alone keeps its function can be obtained securely, easily and efficiently by using the vector of the present invention, in which the selectable marker gene is used in combination with a removable DNA element, the selectable marker gene is positioned such that it behaves integrally with the removable DNA element and the desired gene is positioned such that it does not behave integrally with the removable DNA element. That is, such a tissue can be obtained by simply repeating their selection through the discrimination of morphological changes with the naked eye at the stage of cultured tissue using a generally used medium, and such a plant can be obtained by merely regenerating a plant from the thus selected tissues. When a plurality of genes are introduced into a single plant, this vector can be used repeatedly without limitation by simply changing a part related to each desired gene to be introduced and not changing other constructions including the selectable marker gene.

The present invention will now be illustrated in greater detail with reference to Examples, but it should be understood that the present invention is not construed as being limited thereto.

EXAMPLE 1

I. Construction of Vector

The rbcS promoter present in the chromosome of a tomato (*Lycopersicon lycopersicum* var. Ailsa Craig) was amplified by PCR (primer 1 (rbcS3B1); 5'-GGATGTTAATGGATACTTCTT-3', (SEQ ID NO: 1) primer 2 (rbcS3B2); 5'-GACAATAATTGGTCTCTAGTA-3'), (SEQ ID NO: 2) and the thus obtained fragments were blunt-ended using T4 polymerase (purchased from Takara Shuzo Co., Ltd.) and inserted into the SmaI restriction enzyme site of a plasmid pHSG398 (purchased from Takara Shuzo Co., Ltd.) to obtain a recombinant plasmid pRB1.

Next, the ipt gene obtained by digesting a plasmid pIPT3 (JP-A-9-154580) with BamHI was inserted into the BamHI restriction enzyme site of pRB1 to obtain a plasmid pRB2. The thus obtained plasmid pRB2 was digested with a restriction enzyme EcoRI, the resulting fragment was blunt-ended with T4 polymerase and then a 5'-phosphorylated HindIII linker (purchased from Takara Shuzo Co., Ltd.) was inserted into the site to obtain a plasmid pRB3. The rbcS promoter and ipt gene under the control of the promoter were cut out from the plasmid pRB3 using the restriction enzyme HindIII and inserted into the HindIII restriction enzyme site of a plasmid pBI121 (purchased from TOYOBO), and the thus obtained desired plasmid was named pIPT20.

The plasmid pIPT20 was introduced into *Escherichia coli* JM109, and the resulting strain was applied to international deposition as *E. coli* JM109 (pIPT20) [National Institute of Bioscience and Human Technology, Agency of Industrial Science and Technology, the Ministry of International Trade and Industry (Higashi 1-1-3, Tsukuba-shi, Ibaraki, Japan), international accession number FERM BP-6779, original deposition under Budapest Treaty on Jul. 7, 1999].

Figure 2:
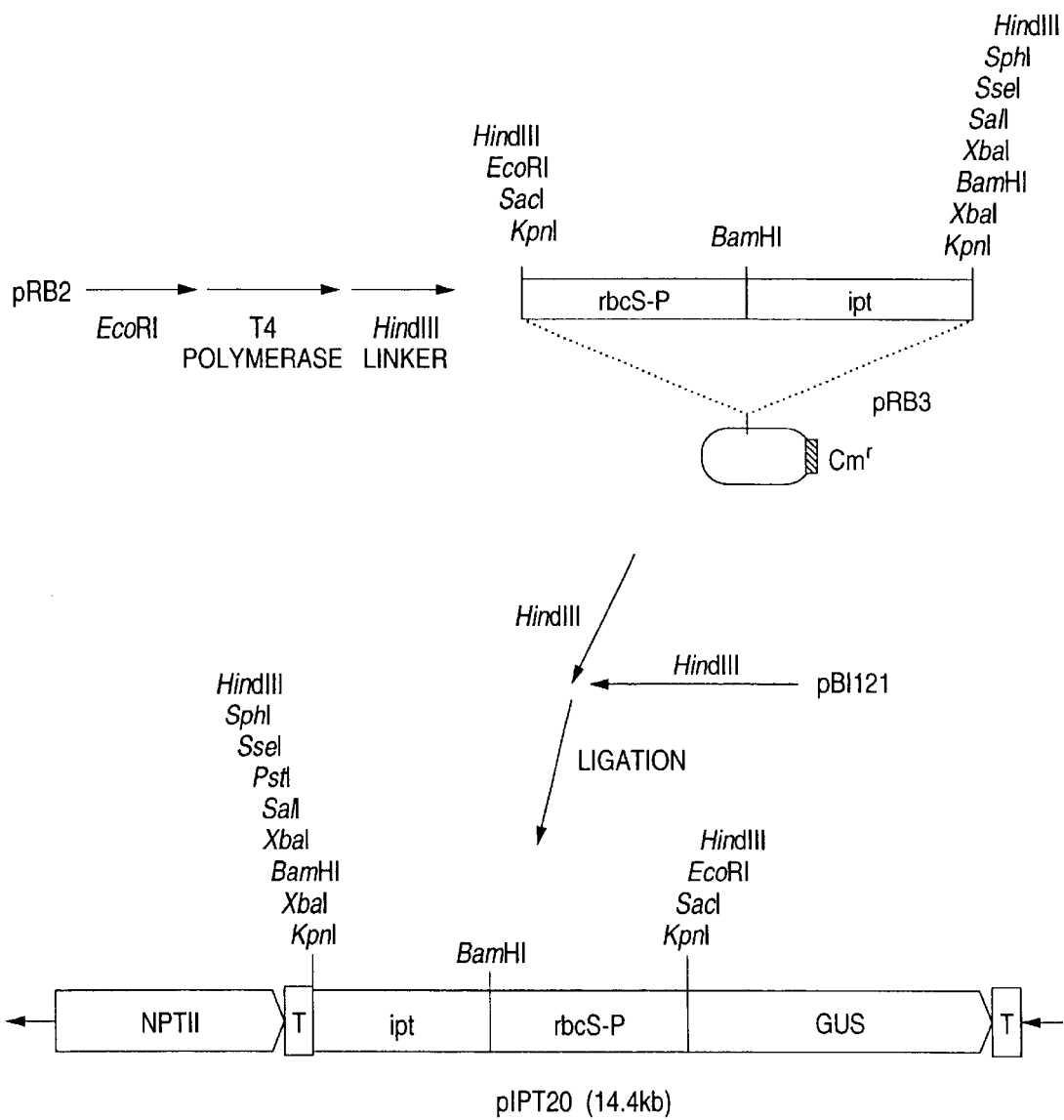
FIG. 2 is a view showing steps until completion of pIPT20 from pRB2 in the pIPT20 construction scheme.

The restriction enzyme map and construction scheme of the T-DNA region of pIPT20 are shown in FIGS. 1 and 2. In these drawings, NPTII, GUS, rbcS-P, and T indicate a kanamycin-resistant gene (neomycin phosphotransferase gene), β-glucoronidase gene, a promoter of a ribulose 2-phosphate carboxylase small subunit gene, which is a light-inducible promoter, and a nopaline synthetase polyadenylation signal, respectively. The small black triangles of arrowhead shape are called RB site (left side of the drawing) and LB site (right side of the drawing), respectively. When the plasmid of this structure is introduced into a plant via *A. tumefaciens*, the region inside of the RB site and LB site is integrated into the plant chromosome. Also, the GUS gene is a gene generally used for the analysis of gene expression in plants, because cells having this gene produce a blue pigment by metabolizing a specific substrate.

As is evident from FIG. 2, this vector plasmid pIPT20 contains the ipt gene as a selectable marker gene, which is an adventitious shoot redifferentiation gene under the control of the light-inducible promoter. Since the cells into which the ipt gene is introduced finally form a tissue having abnormal morphology, an extreme shooty phenotype, which can be clearly judged, transgenic tissues can be easily selected when this gene is used as the selection marker by detecting a tissue which formed the extreme shooty phenotype.

II. Introduction of pIPT20 into Agrobacterium

*A. tumefaciens* strain LBA4404 (purchased from CLON-TECH CO., LTD.) was inoculated into 10 ml of YEB liquid culture medium (containing 5 g/l of beef extract, 1 g/l of yeast extract, 1 g/l of peptone, 5 g/l of sucrose, and 2 mM $MgSO_4$, pH 7.2 at 22° C. (the pH at 22° C. is applied to the following unless otherwise instructed)), and was cultured at 28° C. until $OD_{630}$ was within the range of 0.4 to 0.6. Then, the culture was centrifuged at 6,900×g for 10 minutes at 4° C. to collect the cells. The cells were suspended in 20 ml of 10 mM HEPES (pH 8.0), and the suspension was recentrifuged at 6,900×g for 10 minutes at 4° C. Subsequently, the collected cells were resuspended in 200 μl of 10 mM HEPES, and this suspension was used as a cell suspension for plasmid introduction.

Introduction of pIPT20 into Agrobacterium cells was carried out by mixing 50 μl of the thus prepared cell suspension for plasmid introduction with 3 μl of the pIPT20 prepared in the above step I in a 0.5 ml tube (manufactured by Assist) and then subjecting the mixed solution to electroporation (Gene Pulser II System, manufactured by BIO-RAD). After the electroporation, 200 μl of YEB liquid medium was added to the mixed solution and cultured at 25° C. for 1 hour under stirring, and the thus obtained cells were inoculated onto YEB agar medium (agar 1.5 w/v %, other components are as described above) supplemented with 50 mg/l of kanamycin and cultured at 28° C. for 2 days to form colonies from the cells of *A. tumefaciens*. Introduction of pIPT20 into Agrobacterium cells was confirmed by introducing each of the formed colonies into YEB liquid medium to grow the cells, extracting plasmid from the cells by an alkali method and then amplifying a specified DNA fragment by PCR.

III. Introduction of pIPT20 into Tobacco

A total of 14 discs each having a diameter of about 6 mm were prepared from leaves of tobacco (*Nicotiana tabacum* cv. SR1) which had been aseptically cultured in flasks, and these pieces were used as materials for introducing pIPT20.

That is, each of the thus prepared leaf discs was soaked for about 1 minute in a cell suspension of *A. tumefaciens* strain LBA4404 prepared in the above step II ($OD_{630}$=0.25, the cell density was adjusted by culturing the strain overnight in YEB liquid medium and then diluting the culture broth with sterile water), put on a sterilized filter paper to remove excess cell suspension, bedded on a plant hormone-free MS agar medium (T. Murashige and F. Skoog, *Physiol. Plant.*, 15: 473–497 (1962), supplemented with 2% sucrose and 0.8% agar) to which 40 mg/l of acetosyringone had been added, such that the back side of the leaf turned upward, and then cultured at 25° C. for 2 days in the dark for infection with the strain.

Next, when they were transplanted on the hormone-free MS agar medium supplemented with 500 mg/l of carbenicillin and cultured under light (about 2,500 lux) at 25° C., adventitious shoots were redifferentiated one and a half months later, so that a total of 82 adventitious shoots were cut out from the leaf discs, transplanted on the same medium but containing only 500 mg/l of ticarcillin and cultured under the same conditions for 1 month. Among these adventitious shoots, those which formed extreme shooty phenotype, namely transgenic tissues, after 1 month of the culturing were 72 shoots (87.8%), and the ratio of the thus obtained transgenic tissues per leaf disc was 5.14 tissues per disc. On the other hand, 10 (12.2%) of the cultured adventitious shoots seemed to be grown into gene-non-introduced tissues having normal morphology, because they did not form extreme shooty phenotype after 1 month of the culturing.

Comparative Example 1

Plasmid pBI121 (the marker gene in this case is a kanamycin-resistant gene) was introduced into *A. tumefaciens* strain LBA4404 in the same manner as in Example 1-II, and 15 pieces of tobacco leaf discs were infected with the thus treated *A. tumefaciens* strain LBA4404 in the same manner as in Example 1-III.

When the leaf discs after the infection were cultured on the MS agar medium supplemented with 0.1 mg/l of NAA, 1 mg/l of BA, 100 mg/l of kanamycin and 500 mg/l of carbenicillin at 25° C. under light (about 2,500 lux), adventitious shoots were redifferentiated 2 months later, so that a total of 43 adventitious shoots were cut out from the leaf discs, transplanted on the hormone-free MS agar medium containing 100 mg/l of kanamycin and 500 mg/l of ticarcillin and cultured under the same conditions for 2 month. After 2 months of the culturing on the hormone-free MS medium, 32 (74.4%) of the adventitious shoots showed kanamycin resistance and developed roots, namely formed transgenic tissues, and the ratio of the thus obtained transgenic tissues per leaf disc was 2.13 tissues per disc which was less than half the number of that of Example 1. On the other hand, 11 (25.6%) of the cultured adventitious shoots seemed to be grown into gene-non-introduced tissues, because they did not show kanamycin resistance.

Comparative Example 2

Introduction of a vector into *A. tumefaciens* and tobacco in that order and culturing of leaf discs after the introduction were carried out in the same manner as in Example 1-II and III, except that a plasmid pIPT5 containing cauliflower mosaic virus 35S promoter was used as the vector instead of the plasmid pIPT20 containing rbcS promoter prepared in Example 1.

Adventitious shoots were redifferentiated on the hormone-free MS agar medium from leaf discs infected with pIPT5-introduced *A. tumefaciens* similar to Example 1 but, when these adventitious shoots were cut out 1 month after the *A. tumefaciens* infection and cultured, the ratio of the extreme shooty phenotype formed by the culturing of these adventitious shoots was only 61.6% of the total adventitious shoots redifferentiated after 1 month of the infection, and the ratio was still only 76.4% when the adventitious shoots were cut out and cultured after 2 months of the infection. This means that the ratio of transgenic tissues (which form extreme shooty phenotype when the culturing is continued) to the total adventitious shoots redifferentiated increases as the period of time elapses after infection with *A. tumefaciens*. Nevertheless, the ratio of transgenic tissues to the total adventitious shoots redifferentiated was lower than the case using the light-inducible promoter as the promoter of the adventitious shoot redifferentiation gene.

Comparative Example 3

Introduction of a vector into *A. timefaciens* and tobacco in that order and culturing of leaf discs after the introduction were carried out in the same manner as in Example 1-II and III, except that a plasmid pIPT10 containing the native promoter of ipt gene was used as the vector instead of the plasmid pIPT20 containing rbcS promoter prepared in Example 1.

Adventitious shoots were redifferentiated on the hormone-free MS agar medium from leaf discs infected with pIPT10-introduced *A. tumefaciens* similar to Example 1 but, when these adventitious shoots were cut out 1.5 months after the infection and cultured, the ratio of the extreme shooty phenotype, namely transgenic tissues, formed by the culturing was 71.9% of the total adventitious shoots, and the ratio of the thus obtained transgenic tissues was 4.60 tissues per disc. On the other hand, 28.1% of the thus obtained adventitious shoots seemed to be grown into gene-non-introduced tissues having normal morphology shoots, because they did not form extreme shooty phenotype.

EXAMPLE 2

A stem of a hybrid aspen grown in vitro (*Populus sieboldii×P. grandidentata*) Kitakami Hakuyou Y-63 (collected at an experimental forest of Akita Jujo Chemicals, Co., Ltd.) was cut out to a length of about 5 mm avoiding nodes and further cut vertically in two segments, and the plasmid pIPT20 prepared in Example 1 was introduced as a vector into the stem segments. That is, 40 mg/l of acetosyringone was added to the cell suspension of *A. tumefaciens* LBA 4404 prepared in Example 1, and each of the thus prepared stem segments was soaked for about 1 minute in the cell suspension, put on a sterilized filter paper to remove excess cell suspension, bedded on the MS agar medium which had been modified by changing the nitrogen source composition to 10 mM ammonia-nitrogen and 30 mM nitrate-nitrogen (hereinafter referred to as "modified MS agar medium") and adding 40 mg/l of acetosyringone, and then cultured at 25° C. for 2 to 3 days in the dark for infection with pIPT20-introduced *A. tumefaciens* and thereby introducing pIPT20 into the stem segment.

After 2.5 months, the thus formed adventitious shoots were cut off from the stem segments and cultured on the same medium under the same conditions to distinguish extreme shooty phenotype and normal individuals with the naked eye, and these extreme shooty phenotype and normal individuals were subjected to GUS gene expression test (GUS histochemical assay) in accordance with the method of Jefferson et al.

When the examination was repeated three times using 20 to 24 stem segments as the material, the shoots which formed extreme shooty phenotype were obtained from 45 of the 64 stem segments used (70.3% in gene introduction efficiency calculated based on the expression of ipt gene) and the shoots having GUS activity were obtained from 40 of the segments used (62.5% in gene introduction efficiency calculated based on the expression of GUS gene), thus showing markedly high probability of obtaining transgenic tissues. In this case, the number of the thus obtained transgenic tissues per one stem segment was 3.86 per segment when the formation of the extreme shooty phenotype was used as the index. On the other hand, the ratio of the transgenic tissues to the entire redifferentiated adventitious shoots was 247 tissues per 465 adventitious shoots (53.1%) when the formation of the extreme shooty phenotype was used as the index. Also, 86.8% of the formed extreme shooty phenotype showed GUS activity.

The results are shown in Table 1.

Comparative Example 4

Plasmid pBI121 was introduced into *A. tumefaciens* strain LBA4404 in the same manner as in Example 1-II, and stem segments of the hybrid aspen were infected with the thus introduced *A. tumefaciens* strain LBA4404 in the same manner as in Example 2.

Each of the thus infected stem segments was transplanted on the modified MS agar medium supplemented with 0.5 mg/l of zeatin, 100 mg/l of kanamycin and 500 mg/l of carbenicillin and cultured at 25° C. under light (about 2,500 lux). Although it was able to separate adventitious shoots after 2.5 months of the infection in Example 2, formation of only slight calli and very small adventitious shoots were observed 2.5 months after the infection in this case, so that the culturing was continued for 4 months after infection with *A. tumefaciens* until the adventitious shoots formed on the stem segments grew into a size of 1 to 3 cm.

As a result, adventitious shoots which showed kanamycin resistance and grew into a size of 1 cm or more by the 4 months of culturing after infection with *A. tumefaciens* were obtained from 16 of the 60 stem segments used (26.7% in gene introduction efficiency calculated based on the expression of kanamycin-resistant gene) and shoots having GUS activity were obtained from 13 of the segments used (21.7% in gene introduction efficiency calculated based on the expression of GUS gene), thus showing markedly low probability of obtaining transgenic tissues. In this case, the number of the thus obtained transgenic tissues per one stem segment was 0.35 per segment when kanamycin resistance was used as the index. On the other hand, 85.7% of the adventitious shoots grew into a size of 1 cm or more showed GUS activity, which was almost the same as the number obtained in Example 2.

The results are shown in Table 1.

Comparative Example 5

Introduction of a vector into *A. tumefaciens* and then into hybrid aspen, culturing of the introduced stem segments, and separation and culturing of the adventitious shoots redifferentiated from the stem segments were carried out in the same manner as in Example 2, except that the plasmid pIPT5 used in Comparative Example 2 was used as the vector.

Although adventitious shoots were redifferentiated on the hormone-free medium from the stem segments infected with the pIPT5-introduced *A. tumefaciens* similar to Example 2, the shoots which formed extreme shooty phenotype were obtained from only 25 of 49 stem segments used (51.0% in gene introduction efficiency calculated based on the expression of ipt gene) and the shoots having GUS activity were obtained from 16 of the segments used (32.7% in gene introduction efficiency calculated based on the expression of GUS gene), thus showing lower probability of obtaining transgenic tissues in comparison with Example 2. In this case, the number of the thus obtained transgenic tissues per one stem segment was 0.67 per segment when the formation of the extreme shooty phenotype was used as the index. On the other hand, the ratio of the transgenic tissues to the entire redifferentiated adventitious shoots was very small, namely 33 tissues per 296 adventitious shoots (11.1%), when the formation of the extreme shooty phenotype was used as the index. Also, 62.1% of the formed extreme shooty phenotype showed GUS activity, which was also smaller than that in Example 2.

The results are shown in Table 1.

Comparative Example 6

Introduction of a vector into *A. tumefaciens* and then into hybrid aspen, culturing of the introduced stem segments, and separation and culturing of the adventitious shoots redifferentiated from the stem segments were carried out in the same manner as in Example 2, except that the plasmid pIPT10 used in Comparative Example 3 was used as the vector. Adventitious shoots were redifferentiated on the hormone-free medium from the stem segments infected with the pIPT10-introduced *A. tumefaciens* similar to Example 2, but, similar to Comparative Example 5, the gene introduction efficiency of these stem segments and the selection efficiency of transgenic tissues from them and the ratio of the transgenic tissues in the redifferentiated adventitious shoots were lower than those in Example 2. That is, the shoots which formed extreme shooty phenotype were obtained from 17 of 40 stem segments infected with the pIPT10-introduced *A. tumefaciens* (42.5% in gene introduction efficiency calculated based on the expression of ipt gene), the shoots having GUS activity were obtained from 12 of the segments used (30.0% in gene introduction efficiency calculated based on the expression of GUS gene), and the number of the thus obtained transgenic tissues per one stem segment was 1.00 per segment when the formation of the extreme shooty phenotype was used as the index. On the other hand, the ratio of the transgenic tissues in the entire redifferentiated adventitious shoots was 40 tissues per 292 adventitious shoots (13.7%) when the formation of the extreme shooty phenotype was used as the index. Also, 75.0% of the formed extreme shooty phenotype showed GUS activity.

The results are shown in Table 1.

TABLE 1

Comparison of the performance of marker genes
for gene introduction into hybrid aspen

| Examples Selection criteria | Ex. 1 Adventitious shoot differentiation, extreme shooty phenotype formation (separation after 2.5 months) | | Comp. 5 | Comp. 6 | Comp. 4 Kanamycin resistance (after 4 months) |
|---|---|---|---|---|---|
| Promoter | rbc-S | | 35S | ipt | |
| Gene introduction efficiency | | | | | |
| ipt gene base (%) | 70.3 | | 51.0 | 42.5 | 26.7 |
| transformants (per piece) | 3.86 | | 0.67 | 1.00 | 0.35 |
| GUS gene base (%) | 62.5 | | 32.7 | 30.0 | 21.7 |
| Transformants among shoots (%) | 53.1 | | 11.1 | 13.7 | 100 |
| GUS staining of transformants (%) | 86.8 | | 62.1 | 75.0 | 85.7 |

EXAMPLE 3

The plasmid pIPT20 was introduced into *A. tumefaciens* strain EHA105 (received from ZENECA, England) in the same manner as in Example 1-II, introduction of the vector into hybrid aspen, culturing of the thus introduced stem segments, and separation and culturing of the adventitious shoots redifferentiated from the stem segments were carried out using the resulting strain in the same manner as in Example 2

Adventitious shoots were redifferentiated on the hormone-free medium from the stem segments infected with the pIPT20-introduced *A. tumefaciens* similar to Example 2, and the shoots which formed extreme shooty phenotype were obtained from 45 of the 65 stem segments used (69.2% in gene introduction efficiency calculated based on the expression of ipt gene) and the shoots having GUS activity were obtained from 39 of the segments used (60.0% in gene introduction efficiency calculated based on the expression of GUS gene), thus showing high probability of obtaining transgenic tissues similar to Example 2. In this case, the number of the thus obtained transgenic tissues per one stem segment was 4.43 per segment when the formation of the extreme shooty phenotype was used as the index, which was the most highest value obtained by the gene introduction method of the present invention using hybrid aspen as the material. On the other hand, the ratio of the transgenic tissues to the entire redifferentiated adventitious shoots was also high, namely 288 tissues per 487 adventitious shoots (59.1%) when the formation of the extreme shooty phenotype was used as the index.

EXAMPLE 4

I. Construction of Vector

Figure 3:
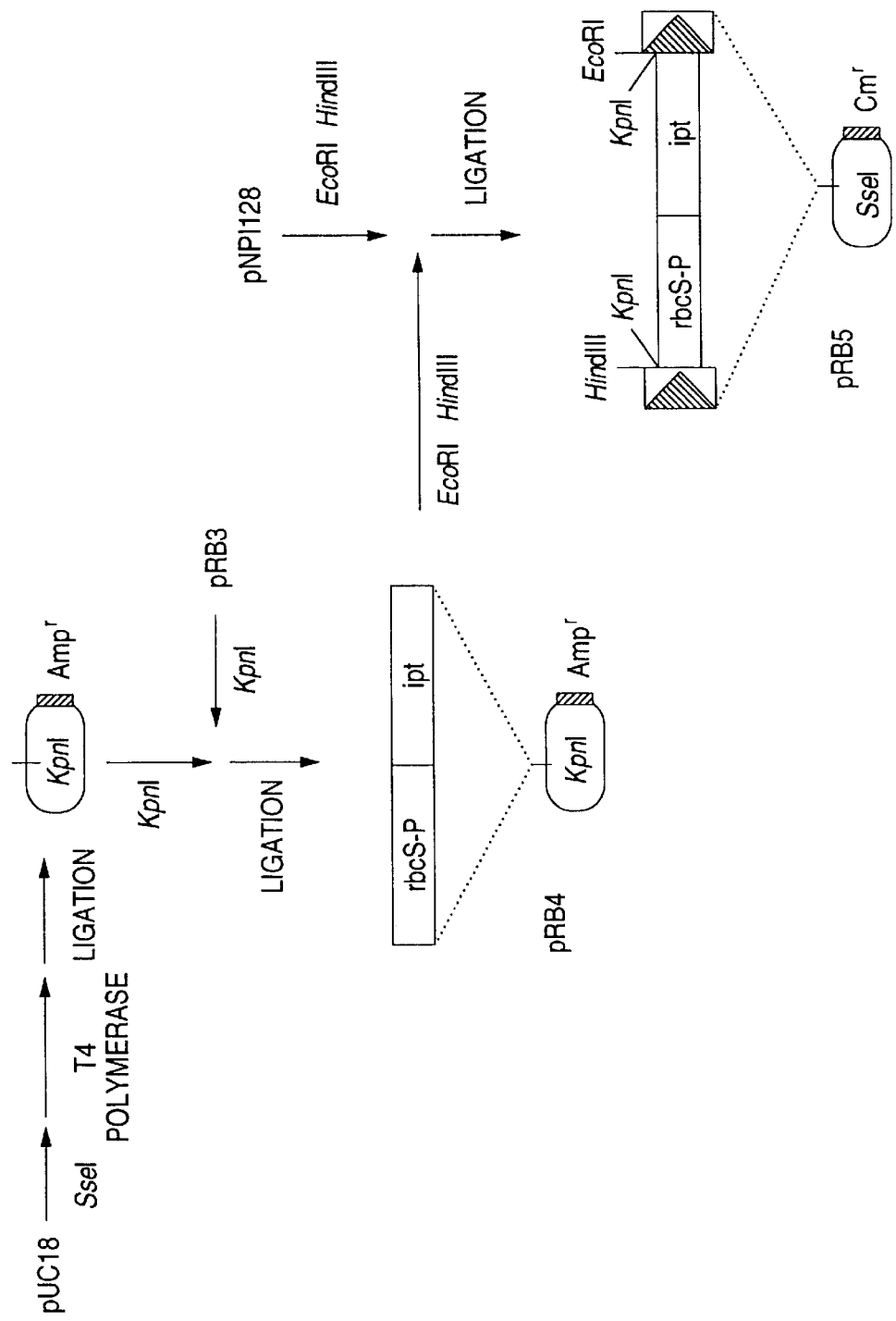
FIG. 3 is a view showing steps until construction of pRB5 from pRB3 in the pRBI11 construction scheme.

The plasmid pUC18 (purchased from Takara Shuzo Co., Ltd.) was digested with a restriction enzyme Sse8387I (hereinafter referred to as "SseI"), and the resulting cohesive ends were blunt-ended with T4 polymerase for self-ligation. The rbcS promoter and ipt gene under the control of the promoter, obtained by cutting off from the plasmid pRB3 with a restriction enzyme KpnI, were once inserted into the KpnI restriction enzyme site of the thus prepared plasmid, and then the rbcS promoter and ipt gene were again cut off therefrom with restriction enzymes EcoRI and HindIII and inserted between the EcoRI-HindIII restriction enzyme sites of a plasmid pNPI128 (JP-A-9-154580), thereby obtaining a plasmid pRB5. The construction scheme of pRB5 is shown in FIG. 3.

On the other hand, principal region of GST-II promoter and a recombinase gene of a yeast site-specific recombination system (pSR1 system), linked to the promoter, were cut off from a plasmid pNPI301 (International Publication No. WO 97/42334) with restriction enzymes EcoRI and XhoI, and the thus cut off DNA fragment was inserted between the EcoRI-XhoI restriction enzyme sites of the plasmid pNPI128 to obtain a plasmid pGSR1. The thus obtained pGSR1 was digested with the restriction enzyme EcoRI, cohesive ends of the fragment were blunt-ended with T4 polymerase, 5'-phosphorylated HindIII linker was inserted between the resulting blunt ends, and then the principal region of GST-II promoter and recombinant enzyme gene linked thereto were again cut off with the restriction enzyme HindIII and inserted into the HindIII restriction enzyme site of pUC18 to obtain a plasmid pGSR2. The construction scheme of pGSR2 is shown in FIG. 4.

The desired plasmid was obtained by inserting the principal region of GST-II promoter and recombinant enzyme gene linked thereto, prepared by cutting off from the plasmid pGSR2 with the restriction enzyme HindIII, into the HindIII restriction enzyme site of pRB5 to prepare a plasmid pRB10 and then inserting a DNA fragment cut off from the pRB10 with the restriction enzyme SseI into the SseI restriction enzyme site of pBI121, and the thus obtained desired plasmid was named pRBI11. The construction scheme of pRBI11 is shown in FIG. 5.

The plasmid pRBI11 was introduced into *Escherichia coli* DH5α, and the resulting strain was applied to international deposition as *E. coli* DH5α (pRBI11) [National Institute of Bioscience and Human Technology, Agency of Industrial Science and Technology, the Ministry of International Trade and Industry (Higashi 1-1-3, Tsukuba-shi, Ibaraki, Japan), international accession number FERM BP-6778, original deposition under Budapest Treaty on Jul. 7, 1999]

Figure 4:
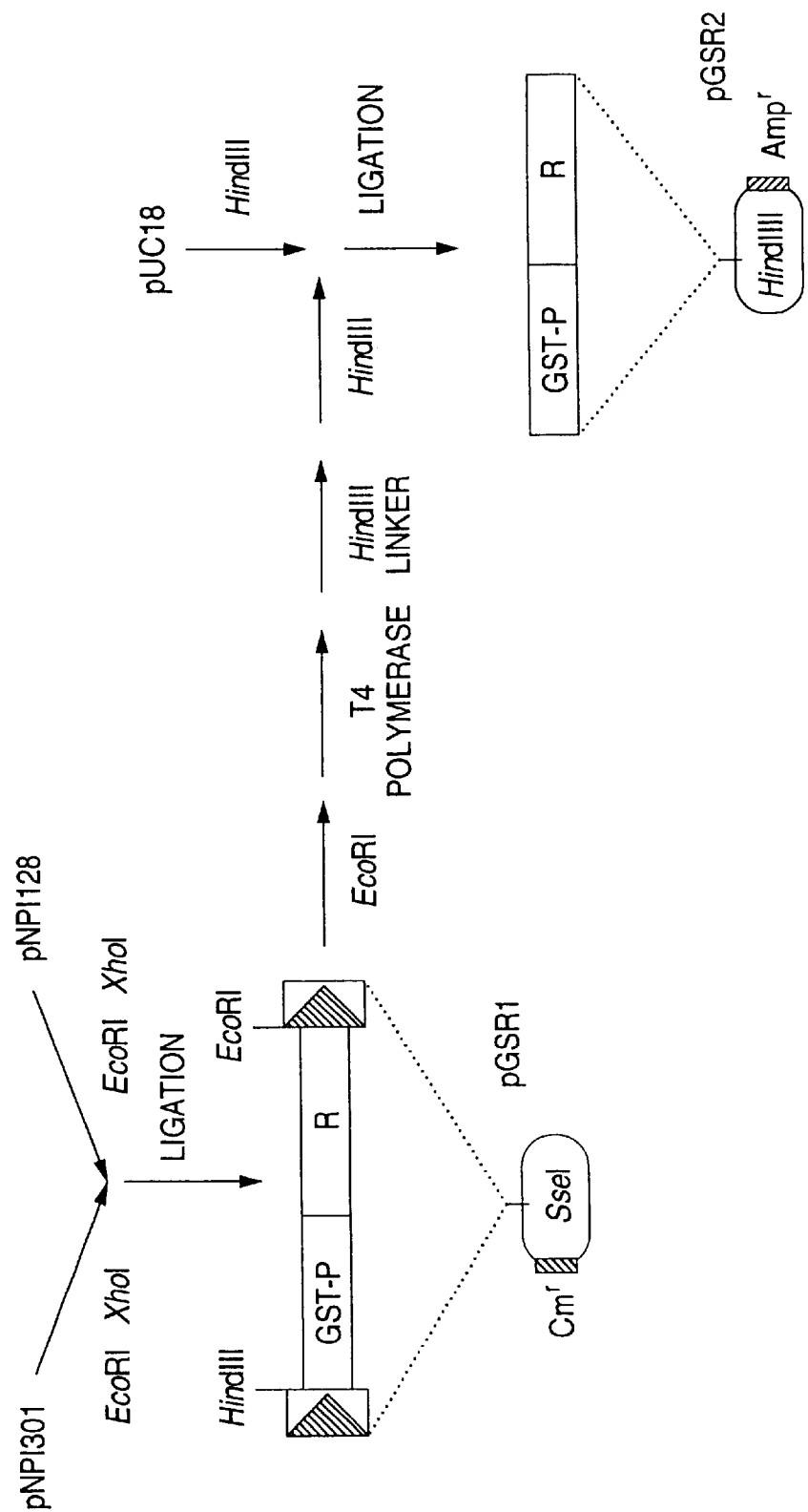
FIG. 4 is a view showing steps until construction of pGSR2 from pNPI301 and pNPI128 in the pRBI11 construction scheme.
Figure 5:
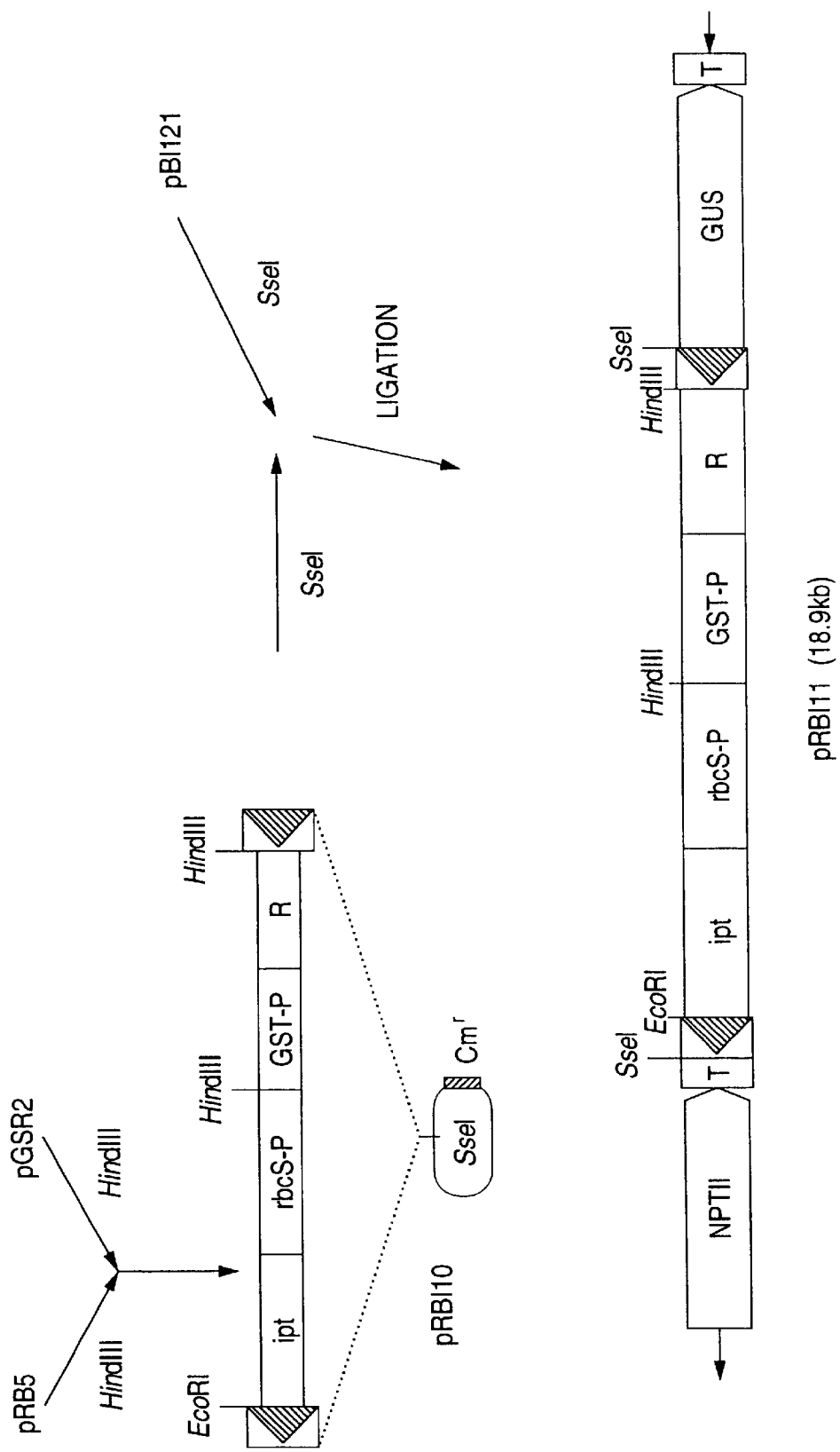
FIG. 5 is a view showing steps until completion of pRBI11 from pRB5 and pGSR2 in the pRBI11 construction scheme.

In FIGS. 3 to 5, GST-P and R indicate the principal region of GST-II promoter and the recombinant enzyme gene of pSRI system, respectively. The GST-II promoter is a promoter of a gene coding for GST-II which is one of the isozymes of GST that participates in the herbicide detoxification, and it is known that GST-P, similar to the GST-II promoter, is activated in the presence of a herbicide antidote, such as 2,2,5-trimethyl-3-(dichloroacetyl)-1,3-oxazolidine or an analog thereof, and thereby dramatically increases expression of a gene under the control thereof, and the inventors confirmed that was also activated when cells containing the same are wound and thereby dramatically increases expression of a gene which is under control thereof. Also, the black triangle with a square frame indicates a recombination sequence RS of the yeast site-specific recombination system and its sequence direction, and the moiety between the recombinant sequences is eliminated by the expression of the recombinant enzyme gene. Other symbols are as used in FIGS. 1 and 2.

As is evident from FIG. 5, the inner region between RB site and LB site is integrated into a plant chromosome when the plasmid pRBI11 is introduced into the plant via A. tumefaciens, similar to the pIPT20 prepared in Example 1-II. However, when the recombinant enzyme gene is expressed thereafter by the activation of GST-P, the selectable marker gene which is present in the region held between the recombination sequences, namely ipt gene under the control of rbcS promoter, is eliminated from the plant chromosome together with the recombinant sequences and recombinant enzyme gene. On the other hand, the desired genes (GUS gene and kanamycin-resistant gene are used as a model in this vector) remain on the chromosome and continue their functions.

II. Introduction of pRBI11 into Hybrid Aspen

In the same manner as in Example 2, the vector pRBI11 prepared in the above step I was introduced into A. tumefaciens and then into stem segments of hybrid aspen, and the stem segments were cultured. When adventitious shoots formed 2.5 months after the A. tumefaciens infection were cut off and again cultured for 1 month using the same medium under the same conditions, adventitious shoots cut off from 14 stem segments among a total of 30 segments formed extreme shooty phenotype, and the extreme shooty phenotype derived from 12 segments among then showed the GUS activity. That is, the gene introduction efficiency calculated based on the expression of ipt gene was 46.7%, and the gene introduction efficiency calculated based on the expression of GUS gene was 40.0%. In this case, all of the thus obtained extreme shooty phenotype showed kanamycin resistance.

Next, in order to express the recombination enzyme gene which should be introduced into the chromosome together with the ipt gene, GUS gene and kanamycin-resistant gene, 9 lines of extreme shooty phenotype derived from respective 9 stem segments were selected from the extreme shooty phenotype showing GUS activity, and each of these tissues was cut into small pieces with a knife to induce the GST-P activity and cultured on the modified MS agar medium which had been supplemented with 0.5 mg/l of zeatin and 500 mg/l of carbenicillin. Since shoots having normal morphology were obtained from 2 lines of extreme shooty phenotype after 2 months of the culturing, they were subjected to GUS histochemical assay and DNA analysis, which confirmed that these shoots have GUS activity and the GUS gene is present in their DNA molecules and also that the ipt gene which should have been present at the time of the extreme shooty phenotype formation was eliminated and disappeared. Additionally, when apical shoots of these shoots were cultured using ⅔ strength MS medium (gellan gum 2.5 g/l) supplemented with 0.05 mg/l of IBA, 200 mg/l of kanamycin and 500 mg/l of carbenicillin, proper development of roots was observed 2 weeks thereafter.

Consequently, it is evident that these shoots obtained from the above-described 2 lines of extreme shooty phenotype are transgenic tissues in which only the desired genes (GUS gene and kanamycin-resistant gene) remain on the chromosome and keep their functions.

The above results confirmed that the introduction of a gene into a plant making use of the vector of the present invention containing a removable DNA element renders possible production of plant tissues in which an adventitious shoot redifferentiation gene used as the selectable marker gene is once expressed but, by the action of the removable DNA element, loses its function thereafter by its removing from the introduced chromosome together with the removable DNA element and, as a result, the desired gene alone remains on the chromosome and keeps its function, and that expression of such a selectable marker gene and disappearance of its function can be detected with the naked eye as morphological changes of the tissues occurred during culturing of the tissues after the gene introduction treatment.

While the invention has been described in detail and with reference to specific examples thereof, it will be apparent to one skilled in the art that various changes and modifications can be made therein without departing from the spirit and scope thereof.

The priority applications, Japanese patent application Nos. Hei 10-202335, filed Jul. 16, 1998, and Hei. 11-197720, filed Jul. 12, 1999, are incorporated herein by reference in its entirety.

What is claimed is:

1. A method for introducing a gene into a plant, which comprises:
   (A) introducing a gene into a plant cell using a vector containing a cytokinin synthesis gene as a selectable marker gene under the control of a light-inducible promoter, and
   (B) selecting a transgenic tissue using, as an index, morphology of an adventitious shoot redifferentiated by expression of the cytokinin synthesis gene which is the selectable marker gene which has been introduced into the plant cell and
   (C) regenerating a plant from said transgenic tissue.

2. The method according to claim 1, wherein the light-inducible promoter is a promoter of a ribulose 2-phosphate carboxylase small subunit gene.

3. The method according to claim 1, wherein the cytokinin synthesis gene is an ipt, isopentenyl transferase, gene which is present in a microorganism belonging to the genus Agrobacterium.

4. A vector for introducing a gene into a plant, which comprises a desired gene, a cytokinin synthesis gene as a selectable marker gene under the control of a light-inducible promoter, and a removable DNA element, wherein the selectable marker is positioned such that it behaves integrally with the removable DNA element, and wherein the desired gene is positioned such that it does not behave integrally with the removable DNA element.

5. The vector according to claim 4, wherein the selectable marker gene is present within the removable DNA element.

6. The vector according to claim 4, wherein the light-inducible promoter is a promoter of a ribulose 2-phosphate carboxylase small subunit gene.

7. The vector according to claim 4, wherein the cytokinin synthesis gene is an ipt, isopentenyl transferase, gene which is present in a microorganism belonging to the genus Agrobacterium.

8. The vector according to claim 6, wherein the removable DNA element is derived from a site-specific recombination system.

9. A plant cell to which the vector of claim 4 has been introduced.

10. A transgenic plant regenerated from the plant cell of claim 9.

11. A plant cell to which the vector of claim 4 has been introduced, wherein said vector has lost the removable DNA element and the selectable marker gene.

12. A transgenic plant regenerated from the plant cell of claim 11.

13. A method for introducing a desired gene into a plant comprising:
   (A) introducing the vector of claim 4 into a plant cell,
   (B) culturing said plant cell under conditions suitable for detecting morphologically abnormal plant tissue,
   (C) selecting at least one cell of said morphologically abnormal plant tissue comprising the desired gene, and
   (D) regenerating a plant from said cell.

14. A transgenic plant produced by the method of claim 13.

15. A method for introducing a desired gene into a plant comprising:
   (A) introducing the vector of claim 4 into a plant cell,
   (B) culturing said plant cell under conditions suitable for detecting morphologically abnormal plant tissue,
   (C) selecting at least one cell of said morphologically abnormal plant tissue comprising the desired gene,
   (D) culturing at least one cell of said morphologically abnormal plant tissue under conditions suitable for detection of normal plant tissue,
   (E) selecting at least one cell of said morphologically normal plant tissue comprising the desired gene, and
   (F) regenerating a plant from said cell.

16. A method for producing a transgenic plant free from the influence of a selectable marker gene, comprising:
   (A) introducing the vector of claim 4 into a plant cell,
   (B) culturing said plant cell into a tissue under conditions suitable for detecting morphologically abnormal plant tissue,
   (C) selecting at least one cell of a said morphologically abnormal plant tissue and culturing it into a tissue under conditions suitable for detecting morphologically normal plant tissue,
   (D) selecting at least one cell of said morphologically normal plant tissue, and
   (E) growing at least one cell of said morphologically normal plant tissue into a transgenic plant.

17. A transgenic plant produced by the method of claim 16.

18. A method for improving redifferentiation efficiency of a transgenic tissue, which comprises introducing a gene into a plant cell using a vector containing cytokinin synthesis gene as a selectable marker gene under the control of a light-inducible promoter.

19. The method according to claim 18, further comprising selecting the transgenic tissue, using as an index, morphology of an adventitious shoot redifferentiated by expression of a cytokinin synthesis gene which is the selectable marker gene which has been introduced into the plant cell.

20. The method according to claim 18, wherein the light-inducible promoter is a promoter of a ribulose 2-phosphate carboxylase small subunit gene.

21. The method according to claim 18, wherein the cytokinin synthesis gene is an Ipt, isopentenyl transferase, gene which is present in a microorganism belonging to the genus Agrobacterium.

* * * * *